United States Patent
Mukkamala et al.

(10) Patent No.: US 8,343,061 B2
(45) Date of Patent: Jan. 1, 2013

(54) METHOD AND APPARATUS FOR DETERMINING CENTRAL AORTIC PRESSURE WAVEFORM

(75) Inventors: Ramakrishna Mukkamala, Lansing, MI (US); Gokul Swamy, East Lansing, MI (US); Qi Ling, Okemos, MI (US); Tongtong Li, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1132 days.

(21) Appl. No.: 12/225,141

(22) PCT Filed: Mar. 15, 2007

(86) PCT No.: PCT/US2007/006465
§ 371 (c)(1),
(2), (4) Date: Sep. 15, 2008

(87) PCT Pub. No.: WO2007/109065
PCT Pub. Date: Sep. 27, 2007

(65) Prior Publication Data
US 2009/0131804 A1    May 21, 2009

Related U.S. Application Data

(60) Provisional application No. 60/782,725, filed on Mar. 15, 2006.

(51) Int. Cl.
*A61B 5/021* (2006.01)

(52) U.S. Cl. ............................................ 600/485

(58) Field of Classification Search .............. 600/485
See application file for complete search history.

(56) References Cited

U.S. PATENT DOCUMENTS 6,647,287 B1    11/2003    Peel, III et al.
2003/0171682 A1    9/2003    Zhang et al.

OTHER PUBLICATIONS

McCombie, D., et al.: "Multi-channel blind system identification of the arterial network using a hemodynamic wave propagation model", American Control Conference, 2004, Proceedings of the 2004 Boston, MA, USA, Jun. 30-Jul. 2, 2004 Piscataway, NJ, USA, IEEE, vol. 2, Jun. 30, 2004, pp. 1645-1646, XP010763123, ISBN: 0-7803-8335-4 (the whole document).

Macombie, D. B., et al.: "Laguerre-model blind system identification: cardiovascular dynamics estimated from multiple peripheral circulatory signals", IEEE Transactions on Biomedical Engineering IEEE USA, vol. 52, No. 11, Nov. 2005, pp. 1889-1901, XP002446120, ISSN: 0018-9294 (abstract).

Sugimachi Masaru, et al: "A new model-based method of reconstructing central aortic pressure from peripheral arterial pressure", Japanese Journal of Physiology, vol. 51, No. 2, Apr. 2001, pp. 217-222, XP002446120, ISSN: 0021-521X (abstract).

*Primary Examiner* — J. E. Angell
(74) *Attorney, Agent, or Firm* — Harness, Dickey & Pierce, P.L.C.

(57) ABSTRACT

A method is provided for determining a central aortic pressure waveform. The method includes: measuring two or more peripheral artery pressure waveforms; analyzing the signals so as to extract common features in the measured waveforms; and determining an absolute central aortic pressure waveform based on the common features.

28 Claims, 5 Drawing Sheets

METHOD AND APPARATUS FOR DETERMINING CENTRAL AORTIC PRESSURE WAVEFORM

CROSS-REFERENCE TO RELATED APPLICATIONS

This application is a U.S. National Stage Application of International application No. PCT/US2007/006465, filed 15 Mar. 2007, and published in English as WO 2007/109065 A1 on 27 Sep. 2007. This application claims the benefit of U.S. Provisional Application No. 60/782,725, filed 15 Mar. 2006. The disclosure(s) of the above applications are incorporated herein by reference.

FIELD

The present disclosure relates to a technique for determining central aortic pressure.

BACKGROUND

As the arterial pressure wave traverses from the central aorta to the peripheral arteries, its contour becomes significantly distorted due to complex wave reflections in the distributed arterial tree. For example, both systolic (maximum) pressure and pulse pressure (systolic minus diastolic (minimum) pressure) usually become amplified, with the extent of the amplification dependent on the particular peripheral site and state of the arterial tree. Thus, it is the systolic and diastolic pressures measured specifically in the central aorta that truly reflect cardiac afterload and perfusion. Perhaps, as a result, central measurements of systolic pressure and pulse pressure have been shown to be superior in predicting patient outcome than corresponding measurements made in more peripheral arteries. Moreover, central aortic pressure is less complicated by wave reflections than peripheral artery pressure, and the entire waveform reveals each systolic ejection phase of a cardiac cycle through the dicrotic notch (which is usually obscured in peripheral artery pressure waveforms) and may be fitted to relatively simple cardiovascular models in order to accurately estimate other clinically important cardiovascular variables such as proportional cardiac output and absolute left ventricular ejection fraction. Thus, methods and apparatus for effectively monitoring the central aortic pressure waveform are extremely desirable in that they would greatly facilitate the monitoring, diagnosis, and treatment of cardiovascular disease.

The central aortic pressure waveform is conventionally measured by introducing a catheter into a peripheral artery and guiding the catheter against the flowing blood to the central aorta. However, placement of a central aortic catheter is not commonly performed in clinical practice because of the risk of blood clot formation and embolization. On the other hand, related, but distorted, peripheral artery pressure waveforms may be measured less invasively and more safely via placement of a catheter in a distal artery. Indeed, radial and femoral artery catheterizations are routinely performed in clinical practice. Moreover, over the past few decades, totally non-invasive methods have been developed and refined to continuously measure peripheral artery pressure based on finger-cuff photoplethysmography and applanation tonometry. These non-invasive methods are even available as commercial systems at present (see, for example, the Finometer and Portapres, Finapres Medical Systems, The Netherlands and the T-Line Blood Pressure Monitoring System, Tensys Medical Inc., San Diego, Calif.). In addition, non-invasive methods are commercially available for measuring signals closely related to peripheral artery pressure waveforms based on photoplethysmography.

Several techniques have therefore been recently introduced to derive the central aortic pressure waveform from related, but distorted, peripheral artery pressure waveforms. The most straightforward of the methods for deriving the central aortic pressure waveform is to measure the peripheral artery pressure waveform at a superficial artery relatively close to the heart (e.g., the carotid artery) in which the wave reflections may be small and simply use this measurement as a surrogate for the central aortic pressure waveform. However, the central aortic and carotid artery pressure waveforms have been shown to be measurably different, especially during systole. But, an even greater drawback of this method is that the carotid artery is not commonly catheterized in clinical practice due to the high level of risk and is a technically difficult site to apply applanation tonometry due to surrounding loose tissue.

Because of the practical difficulty in measuring an arterial pressure waveform relatively near the heart, several mathematical transformation methods have been developed based on a generalized transfer function approach. These methods generally involve 1) initially obtaining simultaneous measurements of central aortic and peripheral artery pressure waveforms (from, e.g., the radial artery) in a group of subjects, 2) estimating a group-averaged transfer function relating the measured peripheral artery pressure waveform to the measured central aortic pressure waveform, and 3) subsequently applying this generalized transfer function to a measured peripheral artery pressure waveform in order to predict the unobserved central aortic pressure waveform. The principal assumption underlying these methods is that arterial tree properties are constant over time and between individuals. However, the wealth of literature concerning the arterial tree indicates that this assumption is not nearly valid. For example, it is well known that the arterial compliance changes with age and disease and that the total peripheral resistance varies greatly under different physiologic conditions. As a result, the generalized transfer function approach can lead to significant discrepancies between estimated and measured central aortic pressure waveforms as well as subsequently derived indices and may be even less accurate in subjects whose measurements were not utilized in the training of the employed generalized transfer function.

A few methods have therefore been more recently developed towards "individualizing" the transfer function relating peripheral artery pressure to central aortic pressure. These methods essentially involve 1) modeling the transfer function with physiologic parameters, 2) estimating a subset of the model parameters from the peripheral artery pressure waveforms and/or other measurements from an individual while assuming values for the remaining parameters, 3) constructing a transfer function based on the estimated and assumed parameter values, and 4) applying the transfer function to the measured peripheral artery pressure waveforms to predict the corresponding central aortic pressure waveform. While these methods attempt to determine a transfer function that is specific to an individual over a particular time period, only a partial individualization is actually obtained. Perhaps, as a result, these methods have found only limited success with results not much, if at all, better than the generalized transfer function approach.

It would be desirable to have an entirely data dependent technique for determining the central aortic pressure waveform from peripheral artery pressure waveforms that is specific to the individual and time period. In this way, the central aortic pressure waveform as well as other important cardiovascular variables could be accurately and continuously monitored with minimally invasive or non-invasive measurement methods. Such a technique could be utilized for hemodynamic monitoring in the intensive care unit, operating room, and recovery room in conjunction with invasive and/or non-invasive peripheral artery pressure transducers as well as in the emergency room, at home, and in the ambulatory setting in conjunction with non-invasive peripheral artery pressure transducers.

The statements in this section merely provide background information related to the present disclosure and may not constitute prior art.

SUMMARY

Methods are provided for determining a central aortic pressure waveform. The methods includes: measuring two or more peripheral artery pressure waveforms; analyzing the signals so as to extract common features in the measured waveforms; and determining an absolute central aortic pressure waveform based on the common features.

In one aspect of this disclosure, the method for determining the central aortic pressure waveform includes: measuring peripheral artery pressure waveforms at more than one peripheral location within an arterial tree of a subject; modeling the arterial tree a single input, multi-output system representing the arterial tree; analyzing the measured waveforms so as to estimate an input of the system to within an arbitrary scale factor; and determining an absolute central aortic pressure waveform by scaling the estimated input based on the measured waveforms.

In another aspect of this disclosure, the method for determining the central aortic pressure waveform includes: measuring peripheral artery pressure waveforms at more than one peripheral location within an arterial tree of a subject; modeling the arterial tree a single input, multi-output system representing the arterial tree; constraining a property of the system; analyzing the measured waveforms so as to estimate an input of the constrained system; and determining an absolute central aortic pressure waveform as the estimated input.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
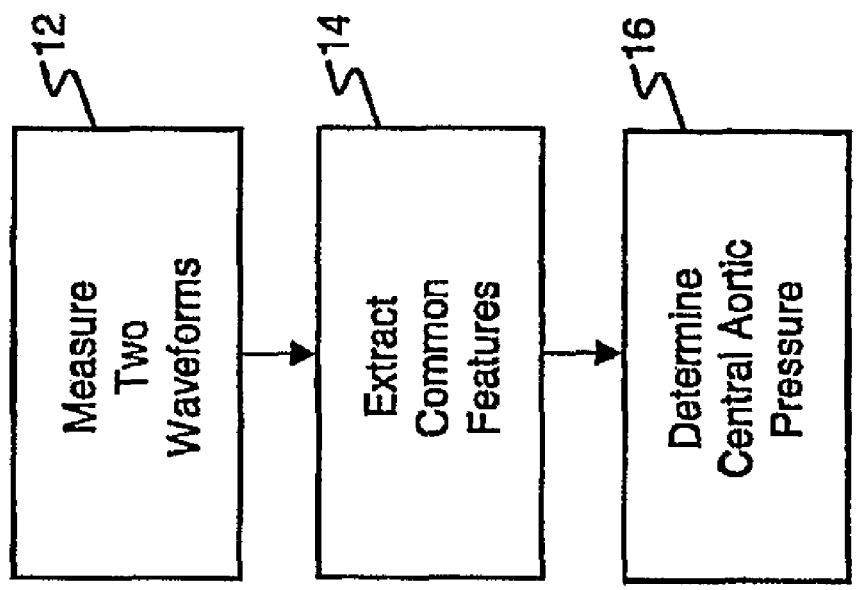
FIG. 1 is a flowchart illustrating an innovative technique for determining central aortic pressure waveform from peripheral artery pressure waveforms.

FIG. 1 illustrates an innovative technique for determining central aortic pressure waveform from peripheral artery pressure waveforms. This technique encompasses the recognition that arterial pressure waveforms measured from different sites in the arterial tree possess common features such as their mean value (due to the cardiac output and global arterial properties including the total peripheral resistance and lumped arterial compliance) and different features (due to complex wave reflections arising from local arterial impedance mismatches). Moreover, the common features of the arterial pressure waveforms provide an accurate representation of the absolute central aortic pressure waveform. The main idea is therefore to determine the absolute central aortic pressure waveform by mathematically analyzing two or more peripheral artery pressure waveforms or related signals so as to extract their common features. An ancillary idea is to then determine the parameters of, and other important cardiovascular variables from, the determined central aortic pressure waveform, which will be less complicated by wave reflections.

Two or more peripheral arterial pressure waveforms or related waveforms are first measured and sampled as indicated at 12. The waveforms may be measured invasively and/or non-invasively using various known techniques. In addition, the waveforms are measured at different peripheral locations. For instance, peripheral arterial waveforms may be measured in the radial arteries and the femoral arteries. Other peripheral locations within the arterial tree are contemplated by this disclosure.

The measured waveforms are then analyzed at 14 so as to extract common features in the waveforms. One way to extract the common features of the measured signals is to first identify the different features and then remove them from the waveforms such that what is left is the common features. An example of this approach is by first estimating the channel impulse responses of a single input, multi-output system which represents an arterial tree of a subject and then deconvolving the estimated impulse responses from the measured waveforms to reconstruct the common input (i.e., the central aortic pressure waveform). Common features may be extracted using other known mathematical analysis techniques. Other exemplary analysis techniques include principal components analysis, independent component analysis, and multi-channel blind system identification in which two or more outputs of a single input, multi-output system are analyzed so as to reconstruct the common unobserved input. Lastly, an absolute central aortic pressure waveform is determined at 16 from the common features.

Figure 2:
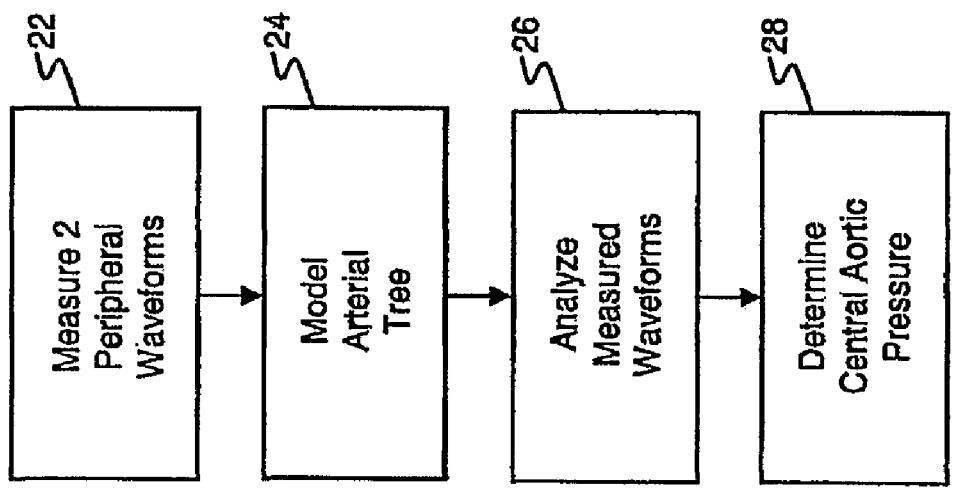
FIG. 2 is a flowchart illustrating a method for determining a central aortic pressure waveform using a single input, multi-output system.

An exemplary embodiment of this technique based on the single input, multi-output system is further described in relation to FIG. 2. First, an arterial pressure waveform is measured and sampled 22 at more than one peripheral location within an arterial tree as noted above. While this exemplary embodiments is based on a single input, multi-output system, it is readily understood that other techniques are also contemplated by this disclosure.

Figure 3:
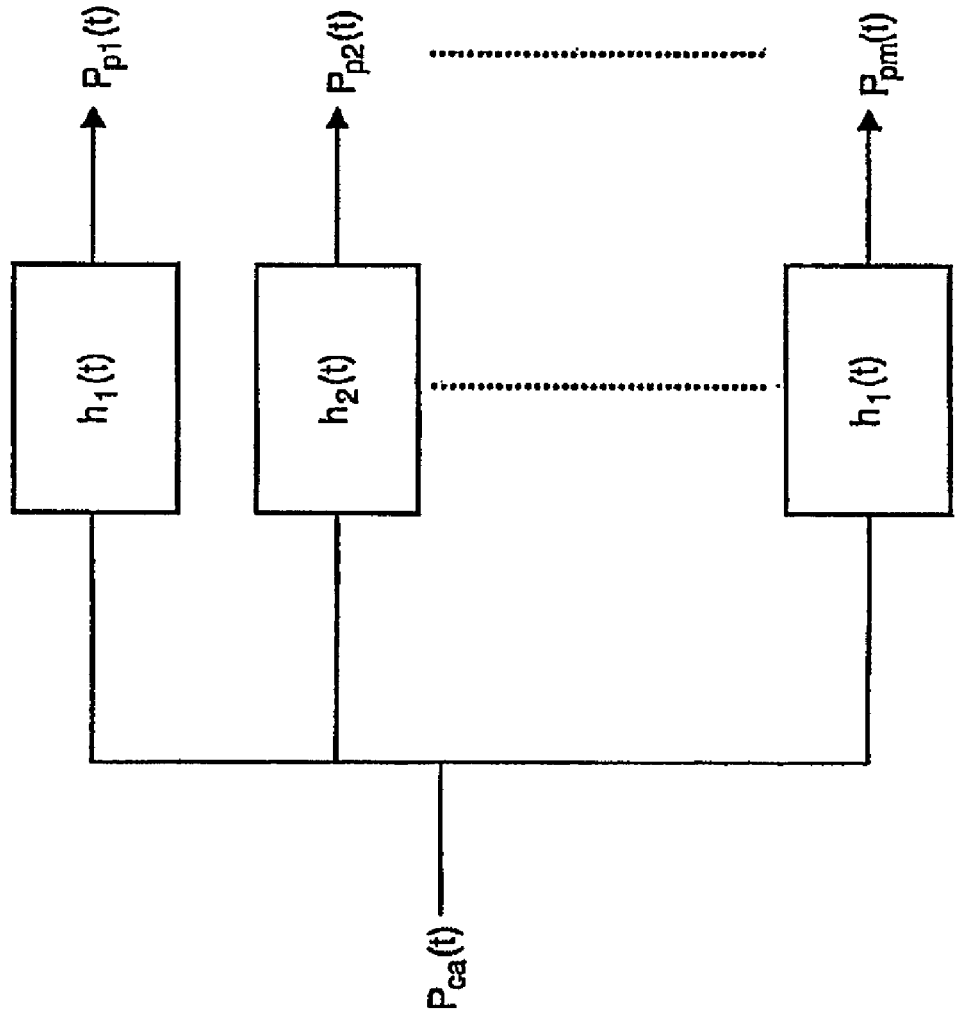
FIG. 3 is a diagram of a single input, multi-output system.

Next, the measured signals are modeled at 24 as outputs in a single input, multi-output system. FIG. 3 illustrates the relationship amongst the pressures at different sites in the arterial tree. In the model, the m outputs of the system ($P_{pi}(t)$, $1 \leq i \leq m$, where m>1) correspond to the m measured and sampled peripheral artery pressure waveforms or related signals, while the common input ($P_{ca}(t)$) represents the unmeasured and likewise sampled central aortic pressure waveform. Each of the discrete-time sub-systems or channels (indicated with blocks) represents the dynamic properties of an arterial tree path coupling the common input to each distinct output. In certain embodiments, the channels are assumed to be linear and time-invariant (LTI) over each time interval of the subsequent mathematical analysis (e.g., from ~15 sec up to a few minutes). Over such short time intervals, the arterial tree is usually operating in near steady-state conditions in which the statistical properties of the pressure waveforms vary little over time. Such steady-state conditions clearly justify a time-invariance approximation while also supporting a linearity approximation as shown in the literature. In certain embodiments, each of the LTI channels is further assumed to be well approximated with a finite impulse response (FIR; $h_i(t)$, $1 \leq i \leq m$). This assumption is well justified, since pressure waveforms from distinct arterial sites only differ significantly in terms of their high frequency detail while being quite similar at lower frequencies. In various embodiments, the channel dynamics (e.g., FIRs in certain embodiments) are assumed to be distinct or coprime (e.g., FIRs possess different zeros), which is necessary for the subsequent step.

With continued reference to FIG. 2, the measured waveforms are then analyzed at 26 so as to estimate the input of the system to within an arbitrary scale factor. In one exemplary embodiment, multi-channel blind system identification techniques are employed to directly reconstruct the central aortic pressure waveform input from the measured waveforms. For example, an input subspace method may be used as is further described in an article by Abed-Meraim, K, W Qiu, Y Hua entitled "Blind system identification" *Proc. of IEEE*, 85(12): 1310-1332, 1997 which is incorporated herein by reference.

In another exemplary embodiment, multi-channel blind system identification techniques are employed to estimate the channel dynamics to within an arbitrary scale factor and then the inverse of the estimated channel dynamics is applied to the measured signals to reconstruct the central aortic pressure waveform to within an arbitrary scale factor. Each of these steps are further described below. In this embodiment, the estimated channel dynamics could be utilized to monitor local arterial functioning at the corresponding peripheral output site. For example, the estimated channel dynamics could be utilized to monitor plaque development in a peripheral artery.

When the channels are assumed to be LTI (or any other input-output relationship that obeys the commutative and associative laws), the channel dynamics may be estimated to within an arbitrary scale factor from the m measured outputs $P_{pi}(t)$ based on the cross relations between pairs of measured outputs. When the LTI channels are further assumed to be well approximated with FIRs, the cross relation between any two measured outputs is specifically given as follows:

$$\sum_{k=0}^{Li} h_i(k) P_{pj}(t-k) = \sum_{k=0}^{Li} h_j(k) P_{pi}(t-k), \tag{1}$$

where $1 \leq i \neq j \leq m$ and Li indicates the duration or order of the $i^{th}$ FIR channel. In preferred embodiments, noise is incorporated into the cross relation equation as follows:

$$e_i(t) = \sum_{k=0}^{Li} h_i(k) P_{pj}(t-k) - \sum_{k=0}^{Li} h_j(k) P_{pi}(t-k), \tag{2}$$

where $e_I(t)$, $1 \leq I \leq m(m-1)/2$, may represent measurement and/or modeling error. For fixed channel orders Li, $1 \leq i \leq m$, the FIRs $h_i(t)$, $1 \leq i \leq m$, are estimated to a certain nontrivial constraint (e.g., the energy of the samples of all the FIRs is set to unity) by minimizing the mean squared value of $e_I(t)$, $1 \leq I \leq m(m-1)/2$ (i.e., least squares methods). This minimization may be solved using a variety of known techniques. For instance, the minimization may be solved in closed-form using the eigenvector method as described by Gurelli et al in "EVAM: an eigenvector-based algorithm for multichannel blind deconvolution of input colored signals" *IEEE Trans. Signal Processing*, 43(1):134-149, 1995 as well as by Xu et al "A least-squares approach to blind channel identification" *IEEE Trans. Signal Processing*, 43(12):2982-2993, 1995. Other exemplary techniques include iteratively with a two-step maximum likelihood method as described by Hua in "Fast maximum likelihood for blind identification of multiple fir channels" *IEEE Trans. Signal Processing*, 44:661-672, 1996; adaptively via a neural network method as described by Dong in "An orthogonal learning rule for null-space tracking with implementation to blind two-channel identification" *IEEE Trans. Circuits Syst. I*, 45:26-33, 1998, or through a numerical search. It is also envisioned that the mean absolute value of $e_I(t)$, $1 \leq I \leq m(m-1)/2$, or any other error criterion may be minimized to estimate the channel dynamics.

Alternatively, the FIRs are estimated based on the properties of the channel subspace rather than the cross relations. For instance, the FIRs are estimated using the filtering matrix as is described by Hua et al in "Blind system identification using minimum noise subspace" *IEEE Trans. Signal Processing*, 45:770-773, 1997; and by Moulines et al. "Subspace methods for the blind identification of multichannel fir filters" *IEEE Trans. Signal Processing*, 43:516-525, 1995. Note, however, that the cross relation and channel subspace methods are very similar and, in fact, identical when m=2. In certain embodiments, the channel orders Li, $1 \leq i \leq m$, are determined using any of the standard methods such as cross validation, cross validation-based criteria, information-based criteria, or singular value analysis (see, Ljung, L. *System Identification: Theory for the User*, PTR Prentice Hall, Englewood Cliffs, N.J., 1987). In certain embodiments, only the maximal channel order ($\max(L_i)$, $1 \leq i \leq m$) is determined using any of these standard methods. In alternative embodiments, the order and parameters of the FIRs are determined jointly as described by Tong et al "Joint order detection and blind channel estimation by least squares smoothing" *IEEE Trans. Signal Processing*, 47:2345-2355, 1999

Prior to their estimation, the FIRs are compactly represented with any set of basis functions. For example, the following truncated exponentially varying sinusoidal basis function representation is used:

$$h_i(t) = \sum_{k=1}^{n} \lambda_{ik}^t (a_{ik} \cos(\omega_{ik} t) + b_{ik} \sin(\omega_{ik} t)), 1 \leq i \leq m, 0 \leq t \leq Li, \tag{3}$$

where $\{\lambda_{ik}, a_{ik}, b_{ik}, \omega_{ik}\}$ are unknown parameters, and n is the number of basis functions. Then, for a fixed number of basis functions n, the parameters are estimated using any of the methods known in the art, including those described above, so as to define the FIRs to within an arbitrary scale factor. For example, after substituting Eq. (3) into Eq. (2), the parameters may be estimated by minimizing the mean squared value of $e_I(t)$, $1 \leq I \leq m(m-1)/2$ (i.e., least squares methods). This parameter estimation may be simplified by making various assumptions about the parameters. For example, $\lambda_{ik}$ may be set to a value based on the value of $\max(Li)$ such as $\exp(-\max(Li)/3)$ (i.e., allowing only a single exponential rate based on the maximum FIR order). As another example, the parameters $\{\omega_{ik}\}$ may be restricted to take on only discrete values according to the Fourier Series (i.e., $2\pi l/L$, where l=0, 1, ..., (LI-1)/2). The number of basis functions may be fixed to a value of one or two or determined with any of various known methods. For example, the number of basis functions may be determined by starting with a single basis function and then adding one basis function at a time until the mean squared value of $e_i(t)$, $1 \leq I \leq m(m-1)/2$, no longer significantly decreases.

When the channels are assumed to be LTI, various method may be used to deconvolve the estimated channels from the measured signals so as to reconstruct the central aortic pressure waveform to within an arbitrary scale factor. In certain embodiments, single-channel deconvolution is applied in which an estimated channel (e.g., $h_i(t)$) is individually deconvolved from its corresponding measured output (e.g., $P_{pi}(t)$) using, for example, standard Fourier techniques or least squares methods with or without regularization. In these embodiments, the single-channel deconvolution is applied to one, some, or all of the estimated channels and corresponding measured outputs to result in multiple versions of the common input Any of these versions of the common input or the average of some or all of them is then selected as the reconstructed central aortic pressure waveform to within an arbitrary scale factor. Alternatively, multi-channel deconvolution is applied in which some or all of the estimated channels are simultaneously deconvolved from the corresponding measured outputs to result in a single common input using, for example, exact methods based on Bezout's theorem as described by Gurelli et al "EVAM: an eigenvector-based algorithm for multichannel blind deconvolution of input colored signals" *IEEE Trans. Signal Processing*, 43(1):134-149, 1995, or least squares methods with or without regularization as described by Abed-Meraim et al "Blind system identification" *Proc. of IEEE*, 85(12):1310-1332, 1997. In certain embodiments, after the deconvolution, a lowpass filter is applied to the reconstructed waveform (with a cutoff frequency set to, for example, 3-10 times the mean heart rate) so as to remove any noise.

An absolute central aortic pressure waveform is determined at 28 by scaling the estimated input based on the measured waveforms. In certain embodiments, the reconstructed waveform is calibrated to absolute pressure based on the measured peripheral artery pressure waveforms. For example, the reconstructed waveform is scaled to have a mean value similar to the mean value of the measured waveforms. This scaling step is well justified, since the paths from the central aorta to peripheral arteries offer very little resistance to blood flow due to Poiseuille's law. Certain embodiments scale the reconstructed waveform to have a mean value specifically equal to that of one of the measured peripheral artery pressure waveforms or the waveform with the largest mean value plus a constant (whose value may be between, e.g., 0 and 3 mmHg). Certain alternative embodiments scale the reconstructed waveform to have a mean value equal to the mean (or medium) of the mean values of some or all of the measured peripheral artery pressure waveforms plus a constant (whose value may be between, e.g., 0 and 3 mmHg).

Figure 4:
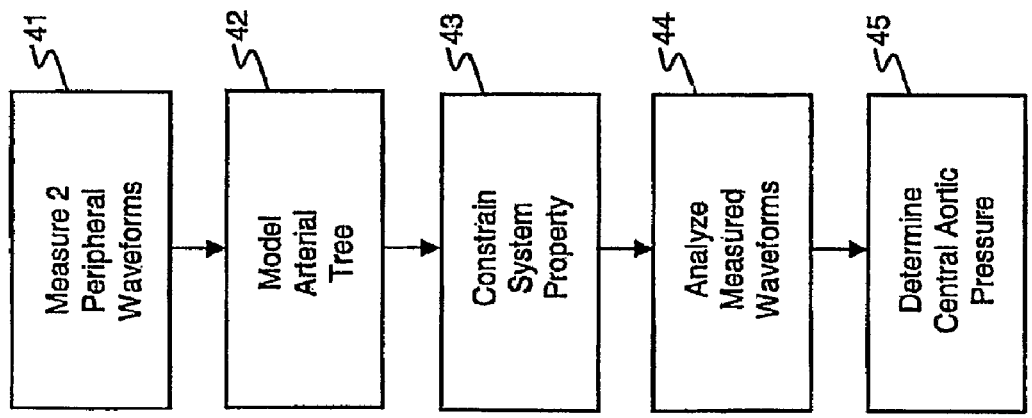
FIG. 4 is a flowchart illustrating an alternative method for determining central aortic pressure waveform.

FIG. 4 illustrates an alternative embodiment. In the alternative embodiment, the reconstructed waveform is calibrated to absolute pressure by constraining 43 a property of the single input, multi-output system and then analyzing 44 the measured signals so as to estimate the absolute central aortic pressure waveform. For example, when the channels of this system are assumed to be LTI, one, some, or all of the channel impulse responses is constrained to a gain near unity. Note that such a constraint permits the channel impulse responses to be estimated exactly (rather to within an arbitrary scale factor) and forces the mean value of the subsequently reconstructed central aortic pressure waveform to be near those of the measured peripheral artery pressure outputs. Another example constrains the gain of a channel by setting the sum of $h_i(t)$ over t to one plus a constant (whose value may be between, e.g., 0 and 0.05). Other parameters as well as other techniques for constraining the system are also contemplated by this disclosure. In any case, the absolute central aortic pressure waveform may be determined by constraining a property of the system and analyzing the measured signals. Lastly, the absolute central aortic pressure waveform is determined 45 as the estimated common input.

In any of these embodiments, the reconstructed absolute central aortic pressure may be used to derive other clinically important cardiovascular parameters. For instance, parameters associated with a central aortic pressure may be derived from the absolute central aortic pressure waveform using any of the known blood pressure detection algorithms. Such parameters include but are not limited to systolic pressure, diastolic pressure, pulse pressure, and/or the systolic ejection phase. Other clinically important cardiovascular variables may also be estimated from the reconstructed absolute central aortic pressure waveform using various known methods. One exemplary method fits a cardiovascular model to the reconstructed waveform. Further details regarding this method are found in U.S. Pat. application No. 12/225/133 entitled "Method and Apparatus for Determining Ejection Fraction" which is filed concurrently herewith and incorporated herein by reference. Exemplary cardiovascular variables include but are not limited to proportional total peripheral resistance, proportional stroke volume, proportional cardiac output, proportional left ventricular end diastolic volume, proportional maximum left ventricular elastance, and/or absolute left ventricular ejection fraction.

Figure 5:
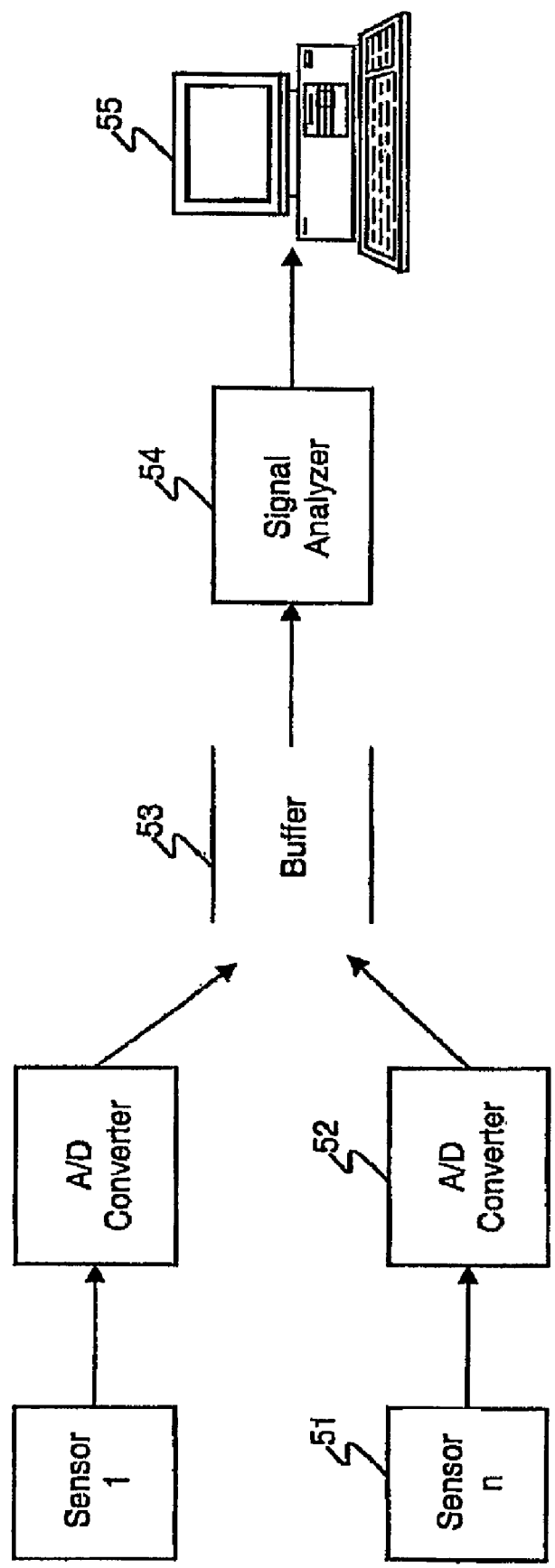
FIG. 5 is a diagram of an exemplary apparatus for implementing the methods of this disclosure.

FIG. 5 illustrates an exemplary apparatus 50 for implementing the methods described above. Two or more sensor 51 measure arterial pressure waveforms or related signals in a subject. Other physiologic signals, such as surface ECGs and a phonocardiogram, may also be input into the apparatus. These signals may be acquired using standard methods and instruments such as those mentioned above. As they are being measured, the signals are fed into a corresponding analog-to-digital converter 52 and then stored in a buffer system 53. The most recent time intervals of the sampled signals (e.g., ~15 sec to a few minutes) are transferred from the buffer system 53 to a signal analyzer 54 (i.e., a processing unit), which analyzes the signals according to the methods described above. The buffer and processing unit may be implemented using, for example, any standard microcomputer running appropriate software to implement the mathematical operations described above. It is to be understood that only the relevant steps of the methodology are discussed above, but that other software-implemented instructions may be needed to control and manage the overall operation of the system. The software components may be coded in any suitable programming language and may be embodied in any of a range of computer-readable media including, but not limited to, floppy disks, hard disks, CDs, zip disks, and DVD disks. Outputs such as the central aortic pressure waveform, the estimated arterial tree channel dynamics, proportional cardiac output, proportional stroke volume, proportional total peripheral resistance, and/or absolute left ventricular ejection fraction may be illustrated on a visual display 55 such as a computer screen and/or may be printed or transmitted to a remote location. The circulatory signals themselves, and analysis thereof, may also be displayed. In a preferred embodiment of the system, the process is continuously repeated thereby providing the on-line monitoring of central aortic pressure, arterial tree channel dynamics, proportional cardiac output, proportional stroke volume, proportional total peripheral resistance, and/or absolute left ventricular ejection fraction (with a small delay due to processing time). Alternatively or additionally, absolute cardiovascular quantities may be computed and displayed by calibrating the proportional cardiovascular estimates via a nomogram or a single absolute measurement of cardiac output (e.g., thermodilution) or ventricular volume (e.g., echocardiography). In certain embodiments, an alarm is triggered upon excessive changes in any of the estimated variables. Finally, the methods may further comprise the step of administering therapy to the subject, or modifying the subject's therapy, based on one or more cardiovascular variables obtained according to the methods and apparatus of the invention.

The above description is merely exemplary in nature and is not intended to limit the present disclosure, application, or uses.

What is claimed is:

1. A method for determining an absolute central aortic pressure waveform comprising steps of:
   measuring peripheral artery pressure waveforms or related signals at more than one peripheral location in an arterial tree of a subject;
   modeling the arterial tree as a single input, multi-output system in which each output corresponds to one of the measured signals;
   constraining a property of the system;
   analyzing, by a computing device having a processor, the signals so as to estimate the absolute common input of the constrained system; and
   determining, by the computing device, the absolute central aortic pressure waveform from the estimated input.

2. The method of claim 1 wherein channels of the constrained single-input, multi-output system model of the arterial tree are first estimated and then an inverse of the estimated channels is applied to the measured signals so as to reconstruct the absolute common input.

3. The method of claim 1 wherein channels of the single-input, multi-output system model of the arterial tree are characterized by linear and time-invariant impulse responses that are coprime.

4. The method of claim 1 wherein one or more of the channels are constrained to unity gain.

5. The method of claim 3 wherein analyzing the measured signals further comprises applying multi-channel blind system identification to the measured signals to estimate parameters and order of the impulse responses and thereby estimate the absolute impulse responses; and estimating the absolute input of the constrained system by deconvolution.

6. The method of claim 5 further comprising the representation of the impulse responses with a set of basis functions with unknown parameters prior to the step of applying multi-channel blind system identification.

7. The method of claim 6 wherein the basis functions are truncated exponential varying sinusoids or truncated polynomials for finite impulse responses.

8. The method of claim 6 wherein the basis functions are complex exponentials for infinite impulse responses.

9. The method of claim 6 wherein the number of basis functions takes on an assumed value or is determined.

10. The method of claim 9 wherein the number of basis functions is determined through mean squared error analysis.

11. The method of claim 10 wherein a subset of unknown parameters of the impulse responses takes on assumed values.

12. The method of claim 5 wherein the parameters and order of the impulse responses are estimated based on cross relations between pairs of measured signals.

13. The method of claim 5 wherein the parameters and order of the impulse responses are estimated based on properties of channel subspace.

14. The method of claim 5 wherein the parameters of the impulse responses are estimated using least squares methods.

15. The method of claim 5 wherein the parameters of the impulse responses are estimated with an eigenvector method, an iterative two-step maximum likelihood method, an adaptive neural network, or a numerical search.

16. The method of claim 5 wherein the orders of the impulse responses take on assumed values or are determined from the measured signals.

17. The method of claim 16 wherein a maximum order of the impulse responses is determined.

18. The method of claim 16 wherein the orders are determined from the measured signals by singular value analysis, cross validation, cross validation-based criteria, or information-based criteria.

19. The method of claim 5 wherein single channel deconvolution is applied to one or more of the estimated impulse responses and corresponding measured signals so as to result in multiple versions of the absolute common input.

20. The method of claim 19 wherein the single channel deconvolution is achieved with Fourier methods or least squares methods.

21. The method of claim 19 further comprising selecting one of the multiple versions as the absolute common input.

22. The method of claim 19 further comprising using an average or median of at least some of the multiple versions as the absolute common input.

23. The method of claim 5 wherein multi-channel deconvolution is applied to one or more of the estimated absolute impulse responses and corresponding measured output signals so as to result in a single absolute common input.

24. The method of claim 23 wherein the multi-channel deconvolution is achieved based on Bezout's theorem or least squares methods.

25. The method of claim 3 wherein the absolute common input of the constrained system is estimated in one step by applying multi-channel blind system identification to the measured signals.

26. The method of claim 25 wherein the estimation is achieved with the input subspace method.

27. The method of claim 1, wherein the estimated absolute impulse responses are utilized to monitor local arterial functioning.

28. The method of claim 1 wherein an absolute central aortic pressure waveform is determined as the estimated common input.

* * * * *